(12) United States Patent
  Pulyassary

(10) Patent No.: US 9,528,935 B2
(45) Date of Patent: Dec. 27, 2016

(54) WATER WEATHER STATION FOR MONITORING CHANGES IN WATER QUALITY

(71) Applicant: Haripriya Pulyassary, Kanata (CA)

(72) Inventor: Haripriya Pulyassary, Kanata (CA)

(*) Notice: Subject to any disclaimer, the term of this patent is extended or adjusted under 35 U.S.C. 154(b) by 232 days.

(21) Appl. No.: 13/775,209

(22) Filed: Feb. 24, 2013

(65) Prior Publication Data

US 2013/0278746 A1   Oct. 24, 2013

Related U.S. Application Data

(60) Provisional application No. 61/618,642, filed on Mar. 30, 2012.

(51) Int. Cl.
  *G01N 21/59*  (2006.01)
  *G01N 21/25*  (2006.01)
  *G01N 21/64*  (2006.01)
  *G01N 21/85*  (2006.01)
  *G01N 21/27*  (2006.01)
  *G01N 21/31*  (2006.01)

(52) U.S. Cl.
  CPC .............. *G01N 21/59* (2013.01); *G01N 21/27* (2013.01); *G01N 21/31* (2013.01)

(58) Field of Classification Search
  CPC ................................ G01N 21/59; G01N 21/27
  USPC .......................................................... 348/81
  See application file for complete search history.

(56) References Cited

U.S. PATENT DOCUMENTS

| 7,454,295 | B2 | 11/2008 | Wolfe |
| 2012/0057782 | A1 | 3/2012 | Bick |
| 2012/0162651 | A1* | 6/2012 | Glover .......................... 356/434 |

* cited by examiner

*Primary Examiner* — Hee-Yong Kim
(74) *Attorney, Agent, or Firm* — Harness, Dickey & Pierce, P.L.C.

(57) ABSTRACT

This invention presents a Water Weather Station system and method for monitoring changes in water quality comprising a water quality monitoring unit, a digital image capturing unit, a digital image processing unit, a water quality display unit, a social media network or cloud collaborative network based water quality data storage, distribution and archiving unit and social media network based communication unit, an automatic water quality classification unit as well as a water quality reporting unit. Various components described in this invention are already well established. The current invention is based on a specific arrangement of these components to develop a Water Weather Station system and a method of using it for monitoring of changes in water quality in any source of water including city water supply, bottled water industry, swimming pools, water theme parks and other arenas where people interact with water resources.

17 Claims, 5 Drawing Sheets

WATER WEATHER STATION FOR MONITORING CHANGES IN WATER QUALITY

CROSS-REFERENCE TO RELATED APPLICATIONS

This application claims priority from U.S. provisional patent application No. 61/618,642, Dated Mar. 30, 2012 entitled "A Social Media Network Based Water Weather Monitoring System For Real Time Monitoring of Changes in Water Quality". The entire content of the application is incorporated herein by reference.

TECHNICAL FIELD

This invention relates to monitoring of changes in water quality in terms of transmission spectrum histograms fingerprints using a spectrophotometer. The invention exploits the power of social media network to provide a relatively inexpensive tool to collect, store, distribute, analyze and report on water quality data irrespective of their geographic location.

BACKGROUND ART

Water contamination through inadvertent or deliberate activities is a serious threat faced by highly populated cities as well as remote villages around the world. Over the years, technology has evolved to analyze the water quality with high degree of precision in terms of various constituents. Such analytical methods are extensively used in water treatment plants around the world. These analytical methods for water quality monitoring are expensive and require high level of technical skills. They are by design intended to assist the water supplier community in adhering to water quality standards. These methods for water quality monitoring are unreachable to the water user community for being used for monitoring of changes in water quality on a daily basis.

Many of the current approaches for water quality monitoring are tightly coupled with expensive and technically complex analytic methods. Without going through these, users can not even detect changes in water quality. In fact, it is an unnecessary burden on water users. In their day to day life, the primary concern of end users is to ensure that the water quality is not changed over time. If they observe any changes in water quality, they have the immediate option to stop using the water. The cause for these changes in water quality is a secondary concern that the user community can address through existing analytical techniques with the help of the water supplier, water supply regulatory authority or public health authority.

Another major limitation of the current approach for changes in water quality monitoring is that the process is implemented in isolation with little or no opportunity for sharing the information. Water contamination is a global phenomenon. Users in different parts of the world encounter similar contamination threats to their water resources. Sharing information on changes in water quality around the world will help users and suppliers for early detection of water quality threats, for identifying optimal solutions and to alert authorities on potentially dangerous situation even before they become reality based on lessons learned from other parts of the world.

U.S. Pat. No. 7,454,295 B2, describes an anti-terrorism water quality monitoring system. This invention combined traditional analytical or electronic monitoring system with a database for storing the data, analyzing module to analyze the result, a computer server and network connectivity to alert authorities if any anomalies are reported. This system could provide the water supplier with better storage, analysis and warning mechanism. But the user community has no direct access to the data collected and stored for immediate decision making in their daily life.

US 2012/0057781 A1 describes another invention for water quality testing using a cell phone application, mirror and plastic bag. This invention could provide individual members of water user community to monitor changes in water quality. However it does not provide any means of sharing the information among the community members.

To bring the water quality monitoring system accessible to the water user community some of the limitations identified above are to be removed. The water quality monitoring system should be affordable and scalable according to the budget available. The storage distribution and archival of the data collected should also be inexpensive and affordable. The collected data should freely be available for the stakeholder community. Steps must be in place for instant notification of the stakeholders if and when changes in water quality are detected. The stakeholder community must be provided with a means of communication to share relevant information on data they collected, contributed or analyzed. Current invention is an attempt to resolve the limitations identified above to provide a Water Weather Station that can detect the changes in water quality and is affordable, scalable and accessible to stakeholders around the world.

SUMMARY OF INVENTION

When light is transmitted through a water sample, some parts of light at some specific wavelengths will be absorbed by the water sample, some parts get scattered and the remaining portion is transmitted. Each element has its own characteristic absorption wavelengths. Thus, changes in the water contaminants will result in changes in the spectrum of the transmitted light, emerging from the water column. Therefore, the light emerging after travelling through the medium will be missing specific wavelengths at which the absorption occurred.

The light emerging from the water sample can be converted into corresponding transmission spectrum using a homemade or commercial off the shelf spectrophotometer. This transmission spectrum image can be photographed using a commercial off the shelf camera and can be converted into image color histogram using standard image processing packages such as ImageJ or Google Picasa. The color histograms associated with the transmission spectrum represents the optical properties of the water sample. Differences in the optical properties of two water samples will result in the differences in the color histogram for the samples.

If the two samples have identical optical properties, the color histograms for the transmission beam spectrum for these samples will be identical. If the optical properties are different due to presence of contaminants, then the color histograms for these samples will be different from each other. Thus, the color histogram produced by a water sample can be used for fingerprinting changes in water quality.

Real time monitoring of the color histogram fingerprints can be used for real time monitoring of changes in the water quality ('water weather'). This monitoring power of water weather station can be further enhanced by providing additional information such as (but not limited to) electrical conductivity, pH, turbidity etc of the water sample.

In the current invention we present a system, apparatus and method for monitoring changes in water quality using the image color histogram fingerprints produced by the transmission spectrum produced by an amateur or commercial off the shelf spectrophotometer. The apparatus can be connected to any water source for continuous real time monitoring of changes in the water quality.

The apparatus exploits the power of Cloud Collaboration Networks such as GoogleDrive, SkyDrive, DropBox and social media networks such as the Google+ and Facebook to upload, store, distribute and archive the transmission spectrum images and their color histogram fingerprints that are accessible from around the world.

An open source Artificial Neural Network based automated data classifier for data visualization and analysis for novice users and experts (http://orange.biolab.si/) is incorporated into the water weather station for classifying the color histogram fingerprint data collected by the Water Weather Station to generate automated alerts and warnings when water quality changes beyond some preset threshold values.

These alerts are sent to the stakeholders through social media and internet based communication medium such as Twitter, Instant Messaging, Message Posting and E-mail. The social media is also used as a means for open communication and discussion among stakeholders in the context of water quality.

BEST MODE FOR CARRYING OUT THE INVENTION

Figure 1:
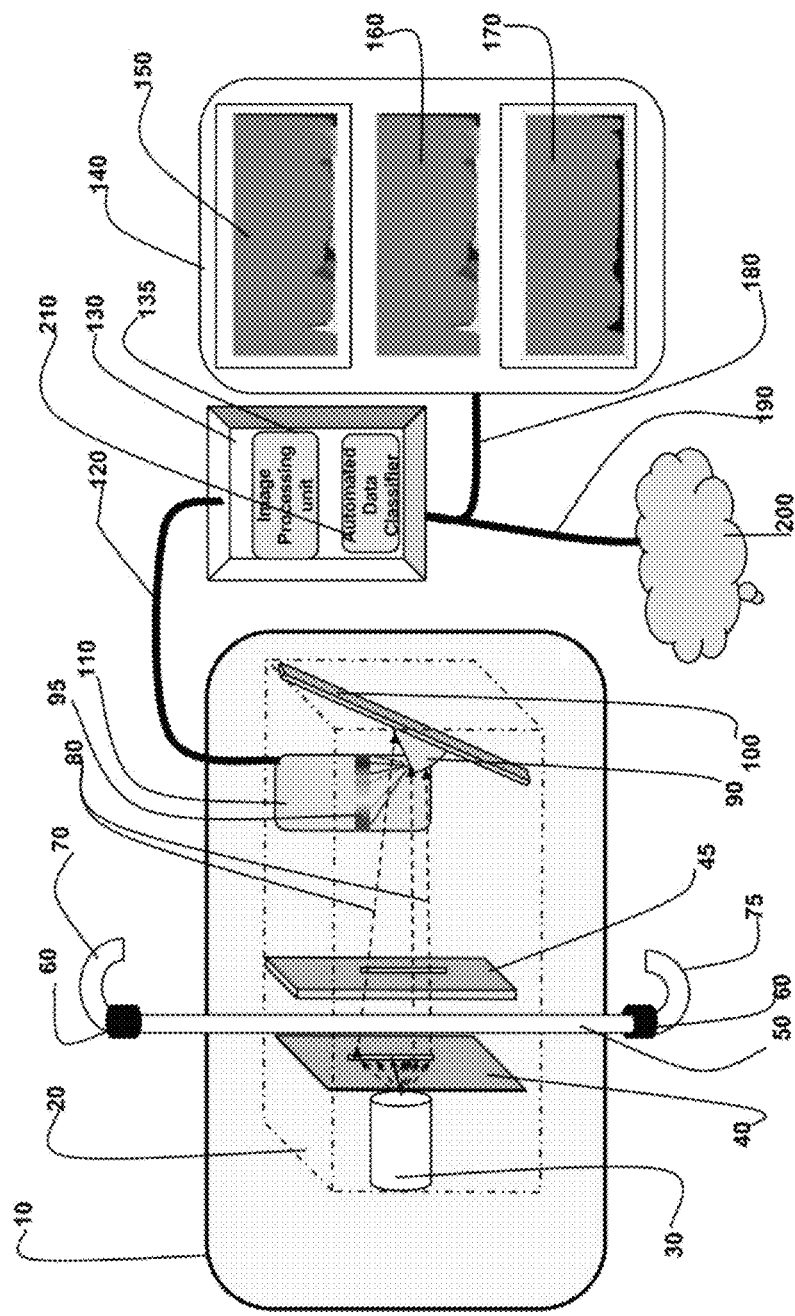
FIG. 1 shows the water weather station and it includes a water quality monitoring unit based on a home-made spectrophotometer, a digital image capturing unit, a digital image processing unit, a water quality display unit, a social media network and cloud collaborative network based water quality data storage, distribution and archiving unit and social media network based communication unit, an automatic water quality classification unit as well as a water quality change reporting unit.
Figure 2:
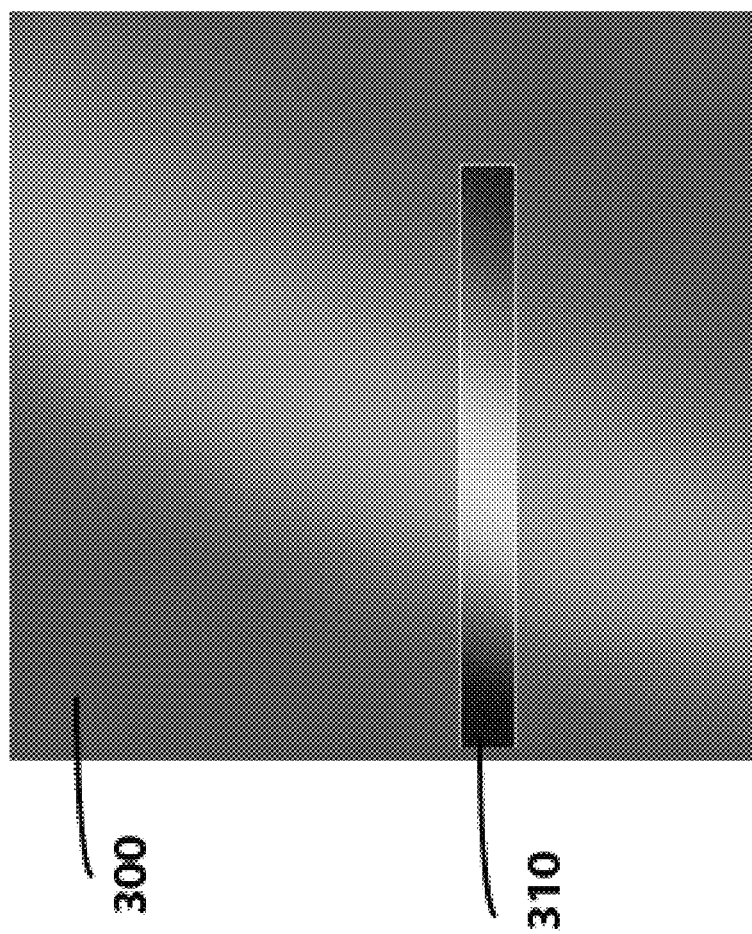
FIG. 2 shows the raw transmission spectrum produced by the spectrophotometer 310 and the cropped segment of the transmission spectrum 320 that will be uploaded to the social/cloud network.
Figure 3:
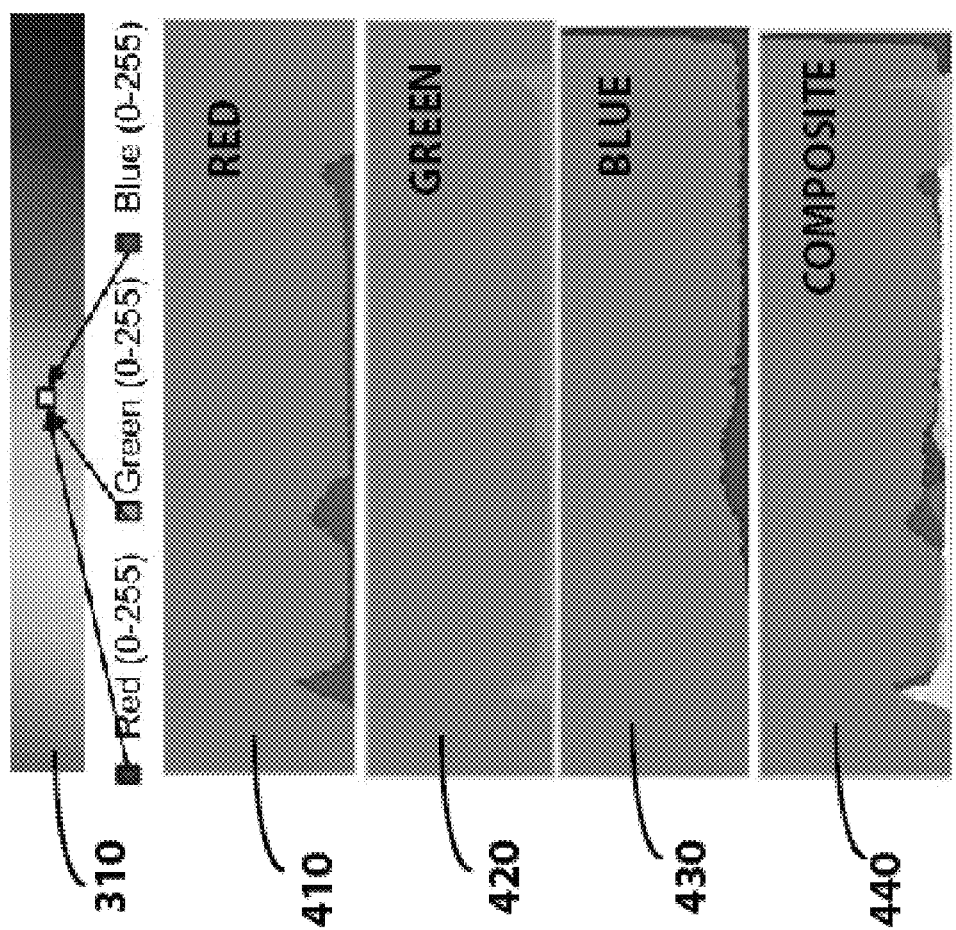
FIG. 3 shows the relationship between the transmission spectrum 310 and the color histogram fingerprints. Each pixel in the transmission spectrum image is represented by a combination of Red, Green, and Blue (RGB) color values; R, G, B color values range from 0-255. The histogram is produced by plotting the number of pixels for each value in the 0-255 range, optionally normalized by the total number of pixels. The histogram fingerprints representing Red 410, Green 420 and Blue 430 are combined to form the composite histogram fingerprint 440.

The home made spectrophotometer 10 consists of a dark chamber 20, light source 30, slit to regulate the incident light on the water column 40, slit to regulate 45 the incident light on the diffraction grating 90 and a removable, transparent container 50 to hold the water sample being tested. The inlet 70 and outlet 75 pipes from the water source are connected to the transparent container holding the water sample 50 using sockets 60.

The light is switched on at desirable intervals (say 5 minutes apart). A light diffraction medium 90 (such as a piece of DVD or a commercial diffraction grating) is placed in the path of the light emerging from the water sample 80 (transmission beam) with the help of a holding platform 100. The diffraction of the emerging light by the diffraction grating produces the transmission spectrum 95, which is captured by a digital camera 110 and transmitted to an image processing unit 135 on a computer 130 connected through wire 120. Generation of color histogram of an image is a standard technique in image processing and is available as part of many commercial and open source image processing packages like ImageJ and Google Picasa. The real time image histogram 160 generated by the image processing unit is displayed on a Histogram Fingerprint Display Unit 140 which could be a standard computer monitor or an LCD screen connected through a wire 180. The Histogram Fingerprint Display Unit may also display a reference Histogram Fingerprint 150 and the difference between the Histograms 170 as the Fingerprint anomaly. This Fingerprint information can be supplemented by displaying additional water quality related information including but not limited to electrical conductivity, pH, turbidity and temperature. The image processing unit is connected to a social media network such as Google+ or YouTube or FaceBook or cloud collaboration network 200 using Internet connection 190. The social media or cloud collaboration network is used by the apparatus for uploading, storing, distributing and archiving water quality Fingerprints around the world. An Artificial Neural Network based automated data classifier 210 is incorporated into the water weather station for classifying the color histogram fingerprint data collected by the Water Weather Station to generate automated alerts and warnings when water quality changes beyond some preset threshold values. These alerts are sent to the stakeholders through social media and internet based communication media such as Twitter, Instant Messaging, Message Posting and E-mail.

The inlet 70 and outlet 75 pipes from the water source are connected to the transparent container holding the water sample 50 using sockets 60. The light is switched on at regular interval (say 5 minutes apart). The light emerging from the sample 80 will be diffracted by the light dispersion medium 90 producing a transmission spectrum that is photographed by the camera 110 and image sent to the image processing unit 135 on the computer 130. The image processing tool set (eg. Google Picasa or ImageJ) will automatically generate the histogram and will be displayed in the color histogram fingerprint 160 along with a reference color histogram fingerprint 150. The reference histogram will be already set by the operator of the water weather station as the color histogram fingerprint corresponding to a reference water source or fingerprint created for a water sample with acceptable quality level based on detailed laboratory testing. The difference between the reference histogram and the real time histogram will be displayed as the histogram fingerprint anomaly 170.

Along with this anomaly information, the operator may choose to display additional water quality information on the histogram fingerprint display unit 140 including, but not limited to, electrical conductivity, pH, turbidity, temperature etc. The real time fingerprint information or its average value over a period (say daily average value), along with additional data resulting from detailed lab tests (whenever available) will be uploaded to an account on the social media or cloud collaborative network 200 such as Google+, Facebook, YouTube, SkyDrive, GoogleDrive and DropBox for storing, distributing and archiving the information. Anyone from around the world with permission to access the account (say through Google+ circle) will be able to access the uploaded data. The Neural Network module 210 will be used to analyze the archived data for identifying patterns and trends in changes in water quality.

Note that various components described in this invention including the spectrophotometer, the light source, camera, diffraction grating, image processing unit, image histogram, histogram fingerprint display unit, the Artificial Neural Network based data classifier and the social media networks such as Google+, Facebook, YouTube are already well established.

The spectral range covered by the histogram fingerprints depends on the capabilities of the spectrophotometer used to produce the transmission spectrum. In the case of a homemade spectrophotometer, the range operation could be extended beyond visible spectral range of (380-700 nm) to include UV (Ultra Violet) and IR (Infra Red) range by the use of an appropriate light source and camera capable of operating in the UV an IR range.

INDUSTRIAL APPLICABILITY

Figure 4:
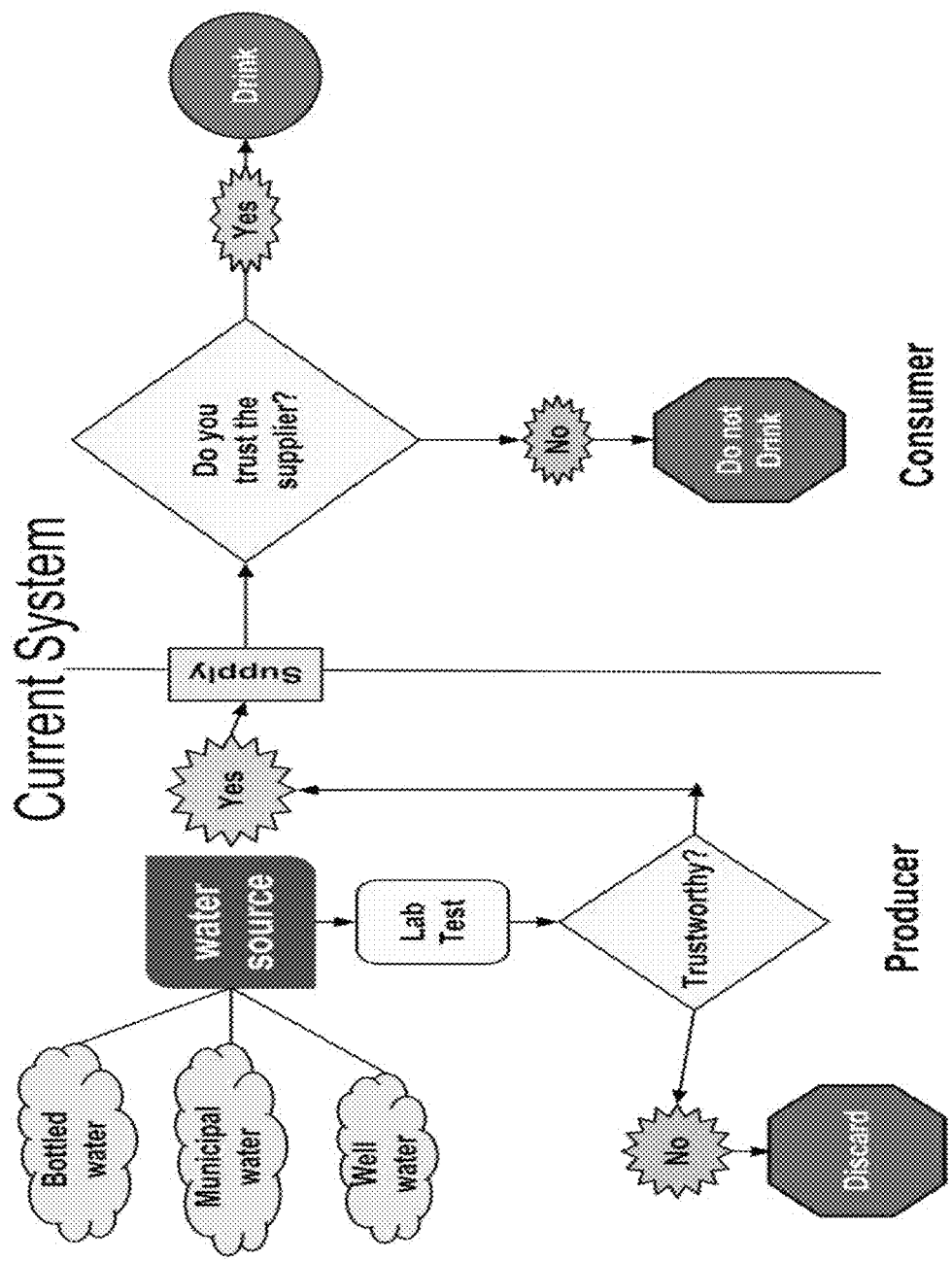
FIG. 4 shows the flow diagram of the current drinking water quality monitoring systems.

FIG. 4 shows the flow diagram of the current drinking water quality monitoring systems. The drinking water producer such as the bottle water supplier, municipal water supplier or the well water supplier conduct mandatory water quality testing required by the regulatory body, periodically (e.g. once every 6 months). Once the water passes this test it is supplied to the consumer. If the consumers implicitly trust the supplier they drink the water. Otherwise discard it.

Figure 5:
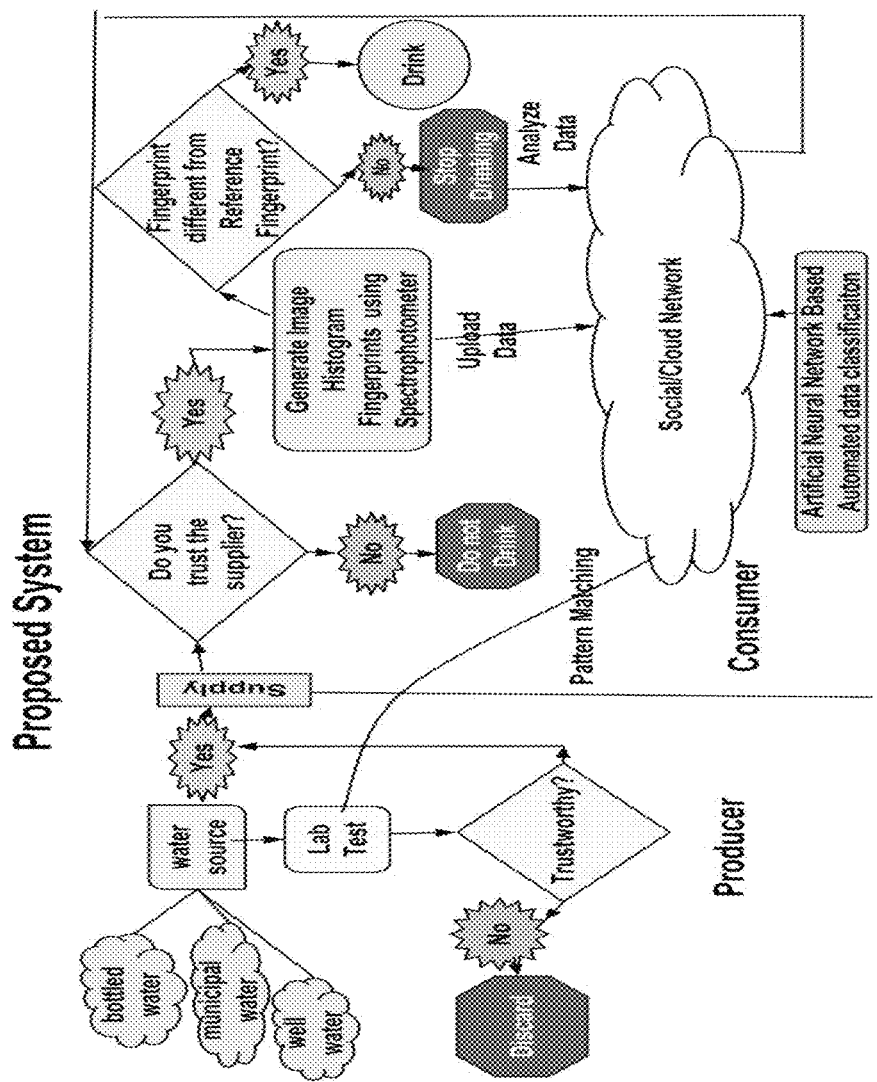
FIG. 5 shows the flow diagram of drinking water quality monitoring systems based on the current invention.

FIG. 5 shows the flow diagram of drinking water quality monitoring system based on the current invention.

Even when the consumer implicitly trusts the supplier, they can use the water weather station to compare and monitor the histogram fingerprints of the water sample against the reference histogram fingerprint. Reference histogram could be provided by the supplier as part of their quality assurance program or generated by the consumers as the long term average of archived fingerprints or could be a fingerprint generated by a quality approved water sample based on detailed laboratory testing.

The transmission spectrum produced as part of the comparison process is uploaded to the social media or cloud collaborative network and is automatically classified using the Artificial Neural Network.

If the histogram fingerprint is different from the reference fingerprint, then, as the first step, the consumer may stop drinking the water.

As an optional second step, the consumer may compare the fingerprints against that available on the social/cloud network to explore any previously reported reason for the difference. If no satisfactory explanation is available, the consumer can contact the supplier for an explanation and for pattern matching of the observed features of the histogram fingerprints against laboratory test results.

The current invention is based on a specific arrangement of these components to develop a Water Weather Station system and a method of using it for monitoring of changes in water quality in any source of water including city water supply, bottled water industry, swimming pools, water theme parks and other arenas where people interact with water resources.

In the case of drinking water supply system, the current invention empowers the consumers with an affordable water quality monitoring tool to monitor their water quality as often as they want and challenge the providers on the quality of the water supply.

In the case of public swimming pools and water theme parks the public health authorities could insist the operators to display the water quality color histogram fingerprints on an hourly basis to ensure that the pools and water theme parks are adhering to a minimum level of hygiene standard. Currently no such mechanism exists to ensure such minimum hygiene standard is always maintained, and a consumer has to just trust the system with no access to the data.

The water quality monitoring unit is flexible enough to accommodate a really affordable homemade spectrophotometer to an expensive compact or large scale commercial spectrophotometer provided they are capable of providing images of transmission spectrum.

The data is stored in the form of images on the social media based or cloud collaboration based networks. Thus it is relatively inexpensive and maintenance free from a consumer's stand point. Also the data is accessible by any member of the social medial or cloud collaborative network provided they have sufficient privileges to access the data.

Thus current invention provides consumers a relatively inexpensive and powerful tool to collect, store, distribute, analyze and report on water quality data any time and as often as they want, irrespective of their geographic location and bring the water quality monitoring to the consumer domain from the producer domain.

CITATION LIST

Patent Literature

U.S. Pat. No. 7,454,295 B2, US 2012/0057781 A1

Non Patent Literature

ImageJ Image processing tool: http://rsbweb.nih.gov/ii/
  Picasa photo editing tool: http://picasa.google.ca/
  Orange Artificial Neural Network Package: http://orange.biolab.si/features/
  Drop Box: http://en.wikipedia.org/wiki/Dropbox_(service)
  Sky Drive: http://en.wikipedia.org/wiki/SkyDrive
  Google Drive: http://en.wikipedia.org/wiki/Google_Drive
  Image Histogram: http://en.wikipedia.org/wiki/Image_histogram

The invention claimed is:

1. A method for monitoring changes in water quality by a water weather station system, wherein the water weather station system includes a water quality monitoring system, a digital image capturing unit, a digital image processing system, a water quality display system, a social media network and a cloud collaborative network based water quality data storage, a distribution and archiving system, a social media network based communication system, an automatic water quality classification system, and a water quality reporting system, the method comprising:
  (a) collecting optical transmission spectrum data corresponding to a water sample that is being monitored as digital images;
  (b) transferring the optical transmission spectrum data through manual or automatic digital file upload to the social media network or the cloud collaborative network for storage, distribution and archiving in a format of digital images;

(c) comparing a number of pixels in each pre-defined optical wavelength range of the optical transmission spectrum data represented in terms of a spectral histogram fingerprint for the water sample being monitored against number of pixels in corresponding wavelength range of the optical transmission spectrum data produced by a reference water sample, represented in terms of a reference spectral histogram fingerprint to evaluate changes in the water quality;

(d) pattern matching the histogram fingerprints against archived fingerprints to infer potential sources of water contamination when detected;

(e) comparing the histogram fingerprints against archived fingerprints from a same water source for trend analysis; and (f) notifying stakeholders including a water user group, a water supplier group, water supply regulatory authorities and public health authorities on potential contamination and trend changes through Internet based and social media based communication means including Instant messages, E-mails, social media message posting and Twitter.

2. The method according to claim 1, wherein the water quality monitoring system of the water weather station system further comprises a spectrophotometer capable of producing a digital image of optical transmission spectrum for the water sample being monitored.

3. The method according to claim 1, wherein the digital image capturing system of the water weather station system consists of a digital image camera or a webcam.

4. The method according to claim 1, wherein the digital image processing system of the water weather station system is configured for processing a raw image of the optical transmission spectrum to standardize a size of the raw image the optical transmission spectrum for computing corresponding color histogram fingerprints as a histogram plot of the number of pixels in pre-defined optical wavelength ranges optionally normalized by a total number of pixels.

5. The method according to claim 1, wherein the automatic water quality classification system of the water weather station system is configured for classifying color histogram fingerprints into various groups based on pattern matching.

6. The method according to claim 1, wherein the water quality display system of the water weather station system is configured for providing visual representation of changes in the water quality in terms of differences in color histogram fingerprints corresponding to water samples being monitored and the reference water sample along with additional water quality information including temperature, conductivity, pH provided by other monitoring sources.

7. The method according to claim 1, wherein the cloud collaborative network based water quality data storage, distribution and archiving system of the water weather station system are configured to upload for storage, distribution and archiving a transmission spectrum digital image, color histogram fingerprints and supplementary information on the water quality including pH, conductivity and temperature.

8. The method according to claim 1, wherein the social media network based water quality data storage, distribution and archiving system of the water weather station system are configured to upload for storage, distribution and archiving with a transmission spectrum digital image, color histogram fingerprints and supplementary information on the water quality including pH, conductivity and temperature.

9. The method according to claim 1, wherein the water quality reporting system of the water weather station system facilitates notifying the stakeholders on the potential water contamination and the trend changes in the water quality through the Internet based and the social media based communication means.

10. The method according to claim 1 further comprising using a spectrophotometer for producing a digital image of optical transmission spectrum corresponding the water sample being monitored.

11. The method according to claim 1 further comprising transferring digital image of the optical transmission spectrum captured by the digital image capturing unit to the social media network and the cloud collaborative network for storage, distribution and archiving.

12. An image processing method according to claim 1 comprising processing a raw image of the optical transmission spectrum to standardize a size of the raw image of the optical transmission spectrum for computing corresponding color histogram fingerprints as a histogram plot of the number of pixels in pre-defined optical wavelength ranges optionally normalized by a total number of pixels.

13. An automated data classification method according to claim 1 comprising classifying color histogram fingerprints into various groups based on pattern matching.

14. A method for displaying water quality information according to claim 1 comprising providing visual representation of changes in the water quality in terms of differences in color histogram fingerprints corresponding to the water sample being monitored and the reference water sample.

15. The method according to claim 1 further comprising uploading, storing, distributing and archiving optical transmission spectrum digital images, color histogram fingerprints and supplementary information on the water quality including pH, conductivity and temperature to a cloud collaboration network.

16. The method according to claim 1 further comprising uploading, storing, distributing and archiving optical transmission spectrum digital images, color histogram fingerprints and supplementary information on the water quality including pH, conductivity and temperature to a social media network.

17. The method according to claim 1 further comprising of notifying the stakeholders on the potential water contamination and the trend changes in the water quality through the Internet based and the social media based communication means.

* * * * *